United States Patent [19]

Gaba

[11] Patent Number: 4,643,185
[45] Date of Patent: Feb. 17, 1987

[54] INTRAOCULAR LENS INSERTION GUIDE
[75] Inventor: Rodolfo Gaba, Simi Valley, Calif.
[73] Assignee: Iolab Corporation, Covina, Calif.
[21] Appl. No.: 656,387
[22] Filed: Oct. 1, 1984
[51] Int. Cl.⁴ ............................................. A61B 17/00
[52] U.S. Cl. .................................................. 128/303 R
[58] Field of Search ...................... 128/303 R, 20, 354, 128/355, 345; 3/13; 623/4, 6

[56] References Cited
U.S. PATENT DOCUMENTS 2,437,812  3/1948  Freel .............................. 128/303 R
4,226,228  10/1980  Shin et al. ............................ 128/20

Primary Examiner—Michael H. Thaler
Attorney, Agent, or Firm—Donal B. Tobin

[57] ABSTRACT

An insertion guide for aiding the insertion of the superior haptic of an intraocular lens into the capsular bag of the eye during intraocular surgery. The guide is made of a thin, flexible material and has a body portion and a flap portion connected by an integral connecting portion which permits the flap to move from the first position folded against the body portion to a second position where the flap is disposed at an acute angle to the body portion so that the flap will act as a backstop to guide the superior haptic of an intraocular lens into the capsular bag. The present invention also relates to the method of inserting an intraocular lens using this guide.

2 Claims, 9 Drawing Figures

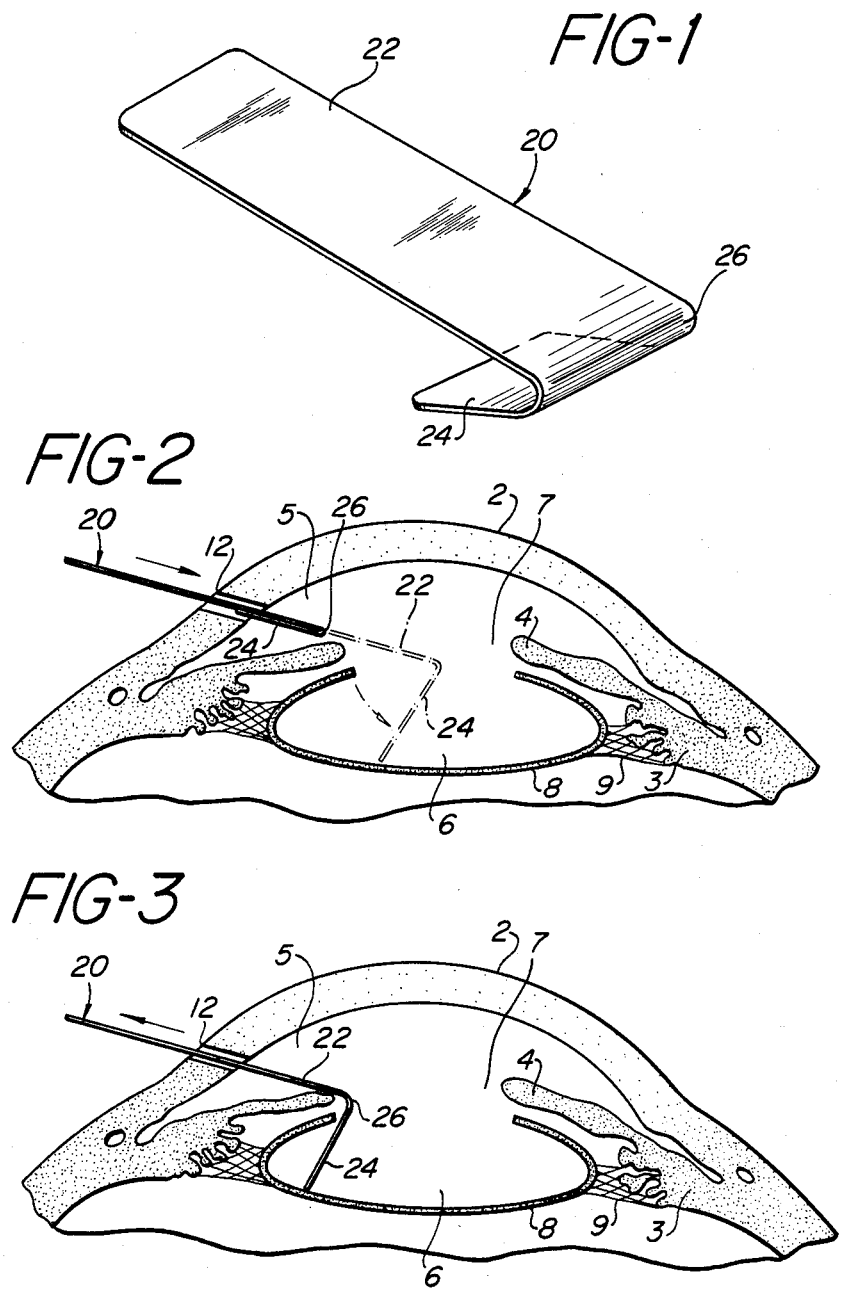

INTRAOCULAR LENS INSERTION GUIDE

FIELD OF THE INVENTION

A device for aiding the insertion of an intraocular lens into the eye and, more particularly, for aiding the insertion of the superior haptic of an intraocular lens into the capsular bag.

BACKGROUND OF THE INVENTION

It is now commonly accepted that the vision impairing disease known as cataracts can be alleviated by surgically replacing the natural lens of the eye with an artificial intraocular lens.

The anatomy of the eye is shown schematically in FIG. 2. The cornea 2 forms the front surface of the eye and connects with the cilliary muscle 3 from which iris 4 extends. Iris 4 divides the front portion of the eye into the anterior chamber 5 in front of iris 4 and the posterior chamber 6, behind iris 4. The pupil 7 is the aperture at the center of iris 4 through which light passes to posterior chamber 6 and onto the back of the eye (not shown).

The condition of cataracts is characterized by the clouding or opacification of the natural lens of the eye so that the amount of light which reaches the retina is substantially reduced or completely eliminated. The natural lens of the eye is encased in a capsular bag 8, as shown in FIG. 2, which is supported by suspensory ligaments, or zonules, 9 from cilliary muscle 3.

During intraocular lens surgery, the natural lens of the eye is removed by a variety of methods well known to those skilled in the art. The front surface of the capsular bag is removed so that an artificial intraocular lens may be placed in capsular bag 8. The eye shown schematically in FIGS. 2, 3 and 5 through 8 has the natural lens and the front surface of capsular bag 8 removed so that the eye is ready for the insertion of the intraocular lens.

There are a wide variety of artificial intraocular lenses that have been used to replace the natural cataract lens. One particularly desirable style of lens is designed to fit completely within capsular bag 8. The type of lens suitable for insertion in the capsular bag is shown in FIG. 4, identified by reference character 10. This lens has two principal parts: a medial, light-focusing body 14 (also called the optic) made of a nontoxic plastic material which will replace the natural lens of the eye and focus light on the retina, and haptic support portions 16 and 18 which extend from optic 14 to the anatomy of the eye and provide means for fixing and holding optic 14 in its proper position within the eye.

Referring again to FIG. 2, there is shown an incision 12 at the edge of the eye through which the lens will be inserted. The patient is usually lying on his back with the doctors standing facing the top of the patient's head. The incision would be made at a position called the superior part of the eye, and the intraocular lens is inserted from the superior portion of the eye toward the inferior portion of the eye. The first haptic to be inserted into the eye is called the inferior haptic. The second haptic to be inserted into the eye is called the superior haptic. This terminology of inferior position and superior position is generally used in the industry, and inferior positions are those spaced further away from the entrance incision, and superior positions are those spaced closer to the entry incision.

When a surgeon inserts an intraocular lens 10, like that shown in FIG. 4, into the eye through incision 12, the inferior haptic is placed against the inferior internal surface of capsular bag 8. The lens is then maneuvered into the capsular bag, and then the superior haptic is placed in capsular bag 8. Many surgeons have difficulty placing the superior haptic in capsular bag 8, because it is very hard to reach and it cannot be easily visualized by the surgeon. Thus, even though the superior haptic may appear to be placed in the superior side of capsular bag 8, it is very difficult to confirm that that is actually the case. It would be desirable if there were an insertion tool that would easily, quickly and reliably permit the surgeon to be assured that he had placed the superior haptic of the lens in capsular bag 8.

SUMMARY OF THE INVENTION

The present invention provides an intraocular lens insertion guide which makes it possible to easily insert the superior haptic of an intraocular lens into capsular bag 8. The lens insertion guide includes a body portion, a flap portion and a connecting portion integrally connecting the body and flap portions. The material of the connecting portion receives a permanent set that permits the flap to be disposed at a predetermined angle with respect to the body portion. The material of the guide is flexible so that the flap may be folded into a first position adjacent the body portion to facilitate insertion of the guide into the eye. The flap opens to a second position after inferior or the distal end of the guide has been inserted through the pupil into capsular bag 8. The guide is then withdrawn superiorly until the flap portion is adjacent the superior portion of capsular bag 8. The lens may be inserted, and the flap portion of the guide acts as a backstop to guide the superior haptic of the intraocular lens into the superior portion of capsular bag 8.

The material of the guide is thin and flexible so that the guide may be easily removed by pulling on the body portion and unfolding the flap so that it is aligned straight with the body portion. Alternatively, a stylus can be introduced through the incision and placed against the back of the flap while the body portion is withdrawn to facilitate unfolding of the flap portion.

In an alternative embodiment, an insertion tube may be placed in the eye, and then the lens guide inserted through the lumen of the tube. This lens tube further facilitates the removal of the lens guide. One merely moves the insertion tube inferiorly until the distal end of the insertion tube abuts the flap portion of the lens guide. The body portion of the lens guide is then retracted through the insertion tube, and the flap is unfolded against the distal end of the insertion tube and then slides out through the insertion tube.

These and other features and advantages of the present invention become more apparent when taken in conjunction with the following detailed description of the preferred embodiments and the following drawings.

BRIEF DESCRIPTION OF THE DRAWINGS

FIG. 1 shows a perspective view of the lens insertion guide of the present invention;

FIG. 2 shows a schematic representation of the forward portion of the eye and the lens insertion guide as it is being inserted into the eye;

FIG. 3 shows the lens insertion guide of FIG. 2 in a different position;

DETAILED DESCRIPTION OF THE PREFERRED EMBODIMENT

Figure 4:
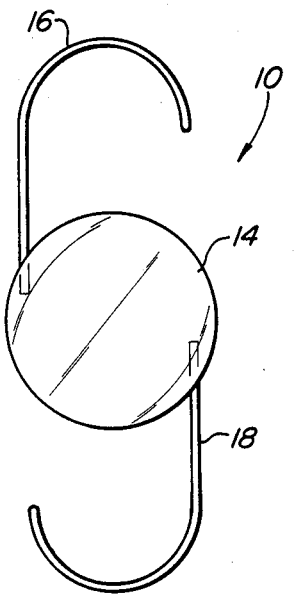
FIG. 4 shows a typical intraocular lens.

Referring now to FIG. 1 there is shown the lens insertion guide 20 of the present invention, including a body portion 22, a flat portion 24 and a connecting portion 26. Guide 20 is preferably made of a thin, flexible material which will not interact with the eye, for example, thin metal like stainless steel or plastic like polyethylene or polypropylene. Guide 20 is preferably about 4 millimeters wide, body section 22 is preferably about 40 millimeters long and flap portion 24 is preferably about 4 millimeters long. The material of guide 20 is preferably about 0.003 inches thick. These materials and dimensions are listed as preferred materials and dimensions for the guide of the present invention and are not intended to limit the present invention to these materials or dimensions.

Guide 20 is preferably manufactured flat, and the edges are trimmed and smoothed so as not to cause any irritation to the eye during use. Guide 20 is then bent at connecting portion 26 to form a permanent set so that in the relaxed condition, flap 24 is disposed at an acute angle with respect to body portion 22, with flap portion 24 being folded back toward body portion 22. The cutting, smoothing and folding operations are performed by well known procedures.

Referring now to FIG. 2, guide 20 of the present invention is used to help insert an intraocular lens into capsular bag 8 of the eye. An incision 12 is made in the edge of the eye, the cataract lens is removed from capsular bag 8 and the inside of capsular bag 8 is cleaned by procedures well known to intraocular surgeons. Guide 20 is inserted through incision 12 with flap 24 folded against body portion 22 with connecting portion 26 entering the wound first. Guide 20 is inserted into the eye past the superior edge of iris 4, into capsular bag 8 and toward the inferior surface of the inside of capsular bag 8. When flap 24 clears the superior edge of iris 4, flap 24 unfolds to assume its relaxed condition (see phantom position in FIG. 2) determined by the permanent set of flap portion 24 with respect to body portion 22.

Referring now to FIG. 3, guide 20 is withdrawn superiorly until connecting portion 26 abuts the superior edge of iris 4.

Figure 5:
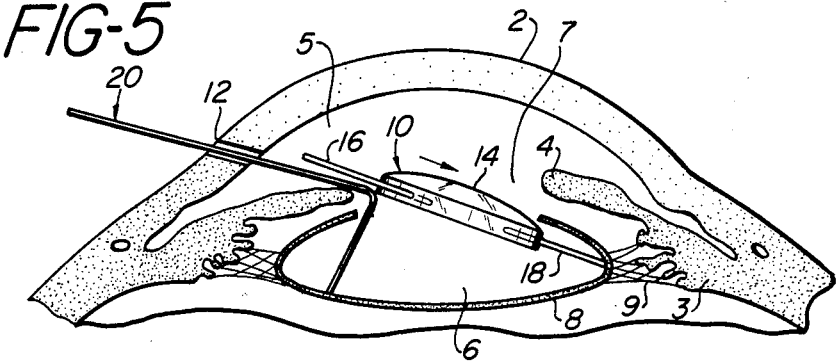
FIGS. 5-7 show an intraocular lens being inserted into the eye using the lens insertion guide of the present invention.
Figure 6:
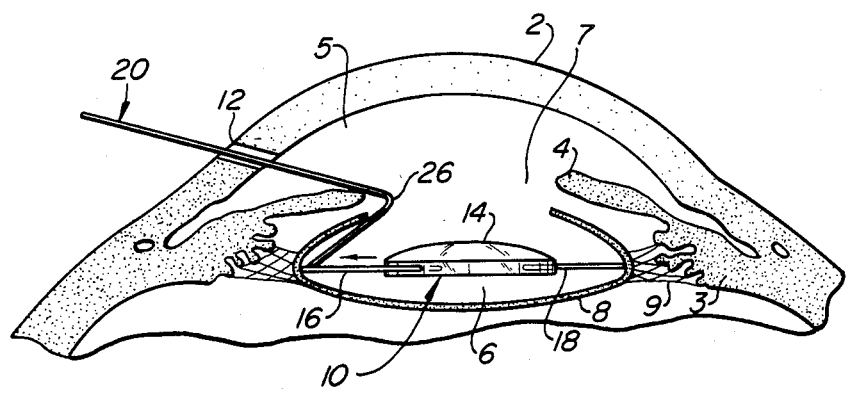

Referring now to FIG. 5, intraocular lens 10 is now inserted through incision 12 along body portion 22 of guide 20 until the inferior haptic 18 of lens 10 abuts the internal inferior surface of capsular bag 8. Lens 10 is then further inserted inferiorly collapsing inferior haptic 18 against the inferior internal surface of capsular bag 8 until optic 14 clears the superior edge of iris 3 and connecting portion 26 of guide 20. Superior haptic 16 is then maneuvered over connecting portion 26 and permitted to slide along flap portion 24 of guide 20 into the superior internal surface of capsular bag 8. Flap portion 24 acts as a backstop to guide superior haptic 16 into its proper position within capsular bag 8. Various surgical instruments may be used by the surgeon to maneuver intraocular lens 10 during the insertion procedure.

Figure 7:
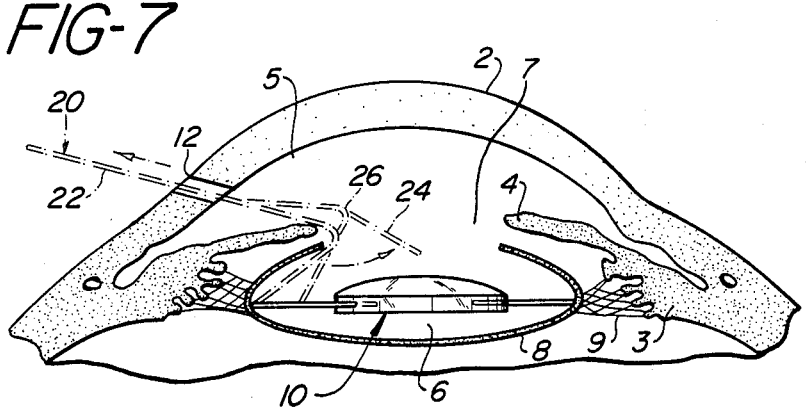

Referring now to FIG. 7, there is shown insertion guide 20 in phantom as it is removed from the eye through incision 12. The surgeon merely grasps body portion 22 of guide 20 and withdraws it slowly from the eye. The force exerted on flap portion 24 by iris 4 or capsular bag 8 will permit flap portion 24 to unfold so that it extends generally in the axial direction from body portion 22. After the removal of insertion guide 20 from the eye, the remaining well known procedures for intraocular lens insertion surgery are performed.

Figure 8:
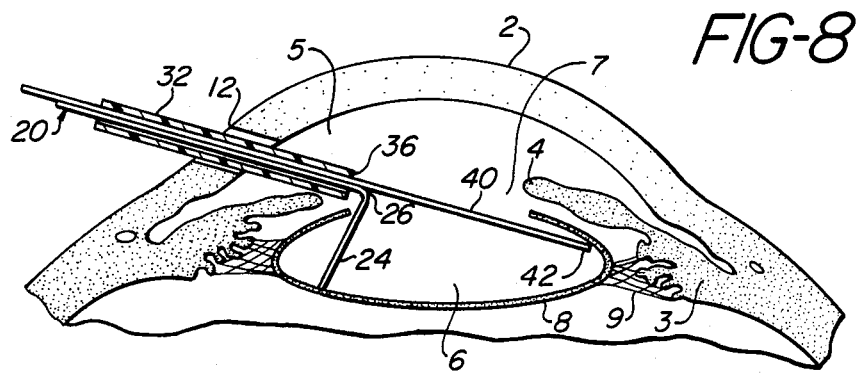
FIG. 8 shows an alternative embodiment of the present invention.
Figure 9:
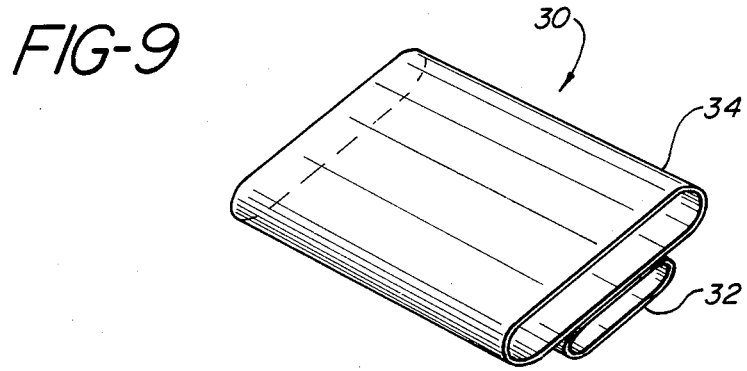
FIG. 9 shows a further alternative embodiment of the present invention.

Referring now to FIGS. 8 and 9, there is shown an alternative method for inserting lens guide 20 into the eye and for removing lens guide 20 from the eye. There is shown in FIG. 9 an insertion device 30 which includes two flat, hollow sections 32 and 34, designated, respectively, as a lens guide insertion tube 32 and a lens insertion tube 34.

Referring now to FIG. 8, there is shown a separate lens guide insertion tube 32 without the lens insertion tube 34 mounted on it. Lens guide 20 may be inserted through the lumen of lens guide insertion tube 32 into the eye until flap portion 24 unfolds, as previously described. Lens guide 20 is then positioned near the superior edge of iris 4, and an intraocular lens can be inserted through incision 12 in the same fashion as previously described. After lens 10 is fully inserted in capsular bag 8, lens guide 20 may be removed by sliding guide insertion tube 32 inferiorly into the eye until the inferior end 36 of guide insertion tube 32 rests in the vicinity of the superior edge of iris 4 and near connecting portion 26 of guide 20. The surgeon then withdraws guide 20 while holding guide insertion tube 32 in position, so that flap portion 24 will pivot about the inferior edge 36 of insertion tube 32. Thus, no additional forces are exerted on the interior anatomy of the eye, particularly on iris 4 and capsular bag 8, during removal of guide 20.

Still referring to FIG. 8, there is shown an alternative method of inserting a lens using a glide 40 much like the well-known Sheets glide. Glide 40 is inserted through the lumen of guide insertion tube 32 either after guide 20 is in place or before guide 20 is inserted into the eye. The inferior edge 42 of glide 40 is directed into the inferior, internal surface of capsular bag 8 to form a ramp along which an intraocular lens may be directed into capsular bag 8. Once the inferior haptic of an intraocular lens is inserted into the inferior portion of the internal surface of capsular bag 8, glide 40 is withdrawn, and the procedure for inserting the superior haptic of the lens is completed as described above.

Referring again to FIG. 9, a lens insertion tube 34 may be piggybacked on guide insertion tube 32 to provide a tube through which the lens itself may be inserted into the eye. With the device shown in FIG. 9, lens guide 20 may be inserted through guide insertion tube 32, as previously described, and then the lens itself may be inserted through lens guide tube 34. Lens guide insertion tube 34 may extend along the complete axial distance of guide insertion tube 32 or it may extend along only a portion thereof.

The present invention has been described in conjunction with certain preferred embodiments. Those skilled in the art will realize that certain modifications and changes may be made to these preferred embodiments without departing from the scope of the present invention. It is, therefore, not intended that the present invention be limited except as set forth in the following claims.

I claim:

1. A lens insertion guide to facilitate the insertion of an intraocular lens into the capsular bag comprising:
   a thin, elongated body portion;
   a thin flap portion;
   a flexible, resilient connecting portion integrally connecting said flap portion and said body portion and permitting said flap to move from a first position, aligned with said body to facilitate insertion of said guide into the eye, to a second position disposed at a predetermined angle to said body portion to act as a backstop to facilitate proper insertion of a lens into the capsular bag;
   wherein said connecting portion permits said flap to move to a third position extending from said connecting portion in a direction away from said body portion and aligned generally parallel therewith to permit the lens guide to be easily removed from the eye; and
   further including a hollow insertion tube for said guide having an axial length shorter than the axial length of said insertion guide so that said flap may be moved from said second position to said third position for removal from the eye by merely pulling said guide through said tube.

2. The lens guide of claim 1 further including a hollow lens insertion tube through whose lumen a lens may be inserted, said lens insertion tube mounted on said hollow guide insertion tube so that said guide and said lens can be inserted into the eye through the different lumens of said guide tube and said lens tube.

* * * * *